United States Patent [19]
Welter et al.

[11] Patent Number: 4,873,350
[45] Date of Patent: Oct. 10, 1989

[54] DISELENOBIS-BENZOIC ACID AMIDES OF PRIMARY AND SECONDARY AMINES AND PROCESSES FOR THE TREATMENT OF DISEASES IN HUMANS CAUSED BY A CELL INJURY

[75] Inventors: André Welter, Beyne-Hevsay, Belgium; Harmut Fischer, Cologne, Fed. Rep. of Germany; Léon Christiaens, Nandrin, Belgium; Albrecht Wendel, Tübingen, Fed. Rep. of Germany; Eugen Etschenberg, Cologne, Fed. Rep. of Germany; Norbert Dereu, Frechen-Bachem, Fed. Rep. of Germany; Peter Kuhl, Bornheim, Fed. Rep. of Germany; Eric Graf, Kerpen-Horrem, Fed. Rep. of Germany

[73] Assignee: A Nattermann & CIE GmbH, Cologne, Fed. Rep. of Germany

[21] Appl. No.: 253,955

[22] Filed: Oct. 3, 1988

Related U.S. Application Data

[63] Continuation of Ser. No. 849,468, Apr. 8, 1986, abandoned.

[30] Foreign Application Priority Data

Apr. 12, 1985 [DE] Fed. Rep. of Germany ....... 3513070
Apr. 12, 1985 [DE] Fed. Rep. of Germany ....... 3513071

[51] Int. Cl.$^4$ .................. C07C 163/00; A61K 31/165; A61K 31/275; A61K 31/245
[52] U.S. Cl. .................................... 549/436; 549/439; 558/415; 560/48; 562/457; 260/550; 514/446; 514/522; 514/535
[58] Field of Search ........................ 260/550; 558/415; 560/48; 562/457; 514/466, 522, 533, 563, 616, 535, 539; 549/436, 439

[56] References Cited

U.S. PATENT DOCUMENTS

3,759,935  9/1973  De Cat et al. .................. 260/550 X
4,352,799 10/1982  Renson et al. ..................... 424/244
4,418,069 11/1983  Welter et al. ...................... 424/269

FOREIGN PATENT DOCUMENTS

98934  1/1984  European Pat. Off. ............ 260/550
2135176 12/1972  France .
 891656 12/1981  U.S.S.R. ............................ 260/550
   2787  6/1914  United Kingdom ................ 260/550

OTHER PUBLICATIONS

Van Caneghem, *Biochemical Pharmacology*, vol. 23, pp. 3491–3500 (1974).
Goble et al., *Antimicrobial and Chemotherapy*, 1967, pp.531–533.
Ivers et al., JCS Perkin I, pp. 2452–2456, (1976).
C. C. Reddy, E. J. Massaro, Fundam. and Appl. Toxicology (3), 9–10, (1983), p. 431–436.
L. Flohe in Free Radicals in Biology, vol. V, Edited by W. A. Pryor, 1982, Academic Press, p. 223–254.
Wendel et al., Biochemical Pharmacology, vol. 31, p. 361 (1982).
Bragt et al., Agents and Actions, Suppl. 17, p. 214 (1980).
L. Flohe et al., The Pharmacology of Inflammation, ed. I. L. Bonta et al., Handbook of Inflammation, vol. 5, Elsevier, Amsterdam, p. 255–270.
H. Rink in "Flutathione", Proceedings of the 16th Conference of the German Society of Biological Chemistry 1973, edited by Flohe, Benohr, Sies, Walter and Wendel, p. 206.
A. Wendel: Methods in Enzymology, vol. 77, p. 325–333 (1981).
A. Wendel, M. Fansel, H. Safayhi, G. Tiegs, R. Otter, Biochem. Pharmac. 33, 3241 (1984).
A. Ruwet, M. Renson, Bull. Soc. Chim. Gelg. 75, p. 157–163.
W. R. Gaythwaite, J. Kenyon, H. Phillips, J. Chem. Soc. 2280 (1928).
J. W. Baker, E. F. C. Banett, W. T. Tweed, J. Chem. Soc. 2831 (1952).

*Primary Examiner*—Charles F. Warren
*Assistant Examiner*—Carolyn S. Greason
*Attorney, Agent, or Firm*—Pearne, Gordon, McCoy & Granger

[57] ABSTRACT

The present invention relates to new diselenobis-benzoic acid amides of primary and secondary amines of the general formula (I):

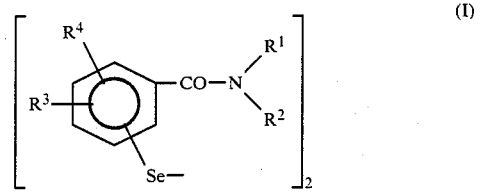

and processes for the treatment of diseases in humans caused by a cell injury.

3 Claims, No Drawings

DISELENOBIS-BENZOIC ACID AMIDES OF PRIMARY AND SECONDARY AMINES AND PROCESSES FOR THE TREATMENT OF DISEASES IN HUMANS CAUSED BY A CELL INJURY

This is a continuation of application Ser. No. 849,468, filed on Apr. 8, 1986 abandoned.

The present invention relates to new diselenobis-benzoic acid amides of primary and secondary amines which are characterized by valuable pharmacological properties and processes for the treatment of diseases caused by a cell injury due to the increased formation of active oxygen metabolites, such as liver defects, cardiac infarction, inflammation, psoriasis, radiation defects.

The compounds of the present invention correspond to the general formula (I):

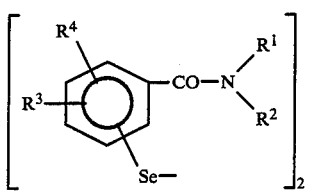

wherein $R^1$ and $R^2$ which are identical or different from each other, represent members selected from the group consisting of hydrogen, straight $C_{1-18}$-alkyl, branched $C_{1-18}$-alkyl, $C_{3-8}$-cycloalkyl, $C_{3-8}$-cycloalkylmethyl, phenylalkyl, phenyl, phenyl substituted by one to three substituents, identical or different from each other, selected from the groups consisting of halogen, $C_{1-4}$-alkyl, $C_{1-4}$-alkoxy, hydroxy, trifluoromethyl, nitro, di-($C_{1-4}$-alkyl)-amino, cyano, carboxy, alkoxycarbonyl, alkoxycarbonylalkyl and methylenedioxy; and together a $C_4$-$C_6$-alkylene bridge, with the proviso that at least one of $R^1$ and $R^2$ is different from hydrogen, and $R^3$ and $R^4$ which are identical or different from each other, represent members selected from the group consisting of hydrogen, halogen, $C_{1-4}$-alkyl, $C_{1-4}$-alkoxy, trifluoromethyl, nitro and together methylenedioxy, the diseleno bridge in the molecule being positioned in the ortho-, meta- or para-position relative to the carbamido group, preferably equally in both rings.

Halogen means fluorine, chlorine, bromine. Alkyl groups having 1–4 carbon atoms are for instance methyl, ethyl, n-propyl, isopropyl, butyl, isobutyl, tert-butyl. Alkoxy groups having 1–4 carbon atoms are for instance methoxy, ethoxy, propoxy and butoxy.

Preferred are compounds wherein $R^1$, $R^2$ are identical or different, but always do not mean hydrogen, and independently represent straight or branched $C_{1-12}$-alkyl, $C_{5-8}$-cycloalkyl, $C_{5-8}$-cycloalkylmethyl, benzyl, phenyl, phenyl substituted by methyl, methoxy or nitro, or together represent a $C_{4-6}$-alkylene bridge and wherein $R^3$, $R^4$ represent hydrogen, fluorine, chlorine, methyl, methoxy, trifluoromethyl or nitro.

In addition, compounds are preferred, wherein $R^1$ represents hydrogen and $R^2$ represents straight or branched $C_{1-18}$-alkyl, $C_{3-8}$-cycloalkylmethyl, benzyl, phenyl, phenyl substituted once to three times independently by fluorine, chlorine, bromine, methyl, methoxy, hydroxy, trifluoromethyl, nitro, dimethylamino, cyano, carboxy, methoxycarbonyl, ethoxycarbonylethyl and methylenedioxy, respectively, and wherein $R^3$, $R^4$ represent hydrogen, fluorine, chlorine, methyl, methoxy, trifluoromethyl, nitro or together represent methylenedioxy.

Within this group, those compounds are preferred wherein the diseleno bridge is in ortho-position to the carbamido group and wherein $R^3$, $R^4$ are identical or different and independently represent fluorine, chlorine, methyl, methoxy, trifluoromethyl, nitro or together represent methylenedioxy, while $R^2$ represents an unsubstituted phenyl group or a phenyl group substituted by hydroxy.

Particularly preferred are compounds wherein $R^3$, $R^4$ are identical or different and independently represent fluorine, chlorine, methyl, methoxy, trifluoromethyl, nitro or together represent methylenedioxy, while $R^2$ represents a straight or branched alkyl group.

Examples for the compounds of the present invention are:

2,2-diselenobis-(N-dimethyl-benzamide)
2,2-diselenobis-(N-diethyl-benzamide)
2,2-diselenobis-(N-di-n-propyl-benzamide)
2,2-diselenobis-(N-diisopropyl-benzamide)
2,2-diselenobis-(N-di-n-butyl-benzamide)
2,2-diselenobis-(N-di-n-hexyl-benzamide)
2,2-diselenobis-(N-di-n-octylbenzamide)
2,2-diselenobis-(N-n-butyl-N-methyl-benzamide)
2,2-diselenobis-(N-n-butyl-N-ethyl-benzamide)
2,2-diselenobis-(N-methyl-N-tert-butyl-benzamide)
2,2-diselenobis-(N-cyclohexyl-N-methyl-benzamide)
2,2-diselenobis-(N-benzyl-N-methyl-benzamide)
2,2-diselenobis-(N-benzyl-N-ethyl-benzamide)
2,2-diselenobis-(N-methyl-N-phenyl-benzamide)
2,2-diselenobis-(N-methyl-N-4-methoxyphenyl-benzamide)
2,2-diselenobis-(N-ethyl-N-3-methylphenylbenzamide)
2,2-diselenobis-(N-ethyl-N-2-nitrophenyl-benzamide)
2,2-diselenobis-(N,N-tetramethylene-benzamide)
2,2-diselenobis-(N,N-pentamethylene-benzamide)
3,3-diselenobis-(N-dimethyl-benzamide)
3,3-diselenobis-(N-diisopropyl-benzamide)
3,3-diselenobis-(N-benzyl-N-methyl-benzamide)
3,3-diselenobis-(N-methyl-N-phenyl-benzamide)
3,3-diselenobis-(N,N-pentamethylene-benzamide)
4,4-diselenobis-(N-dimethyl-benzamide)
4,4-diselenobis-(N-diethyl-benzamide)
4,4-diselenobis-(N-diisopropyl-benzamide)
4,4-diselenobis-(N-benzy-N-methyl-benzamide)
4,4-diselenobis-(N-methyl-N-phenyl-benzamide)
3,3-diselenobis-(N-methyl-benzamide)
3,3-diselenobis-(N-ethyl-benzamide)
3,3-diselenobis-(N-isopropyl-benzamide)
3,3-diselenobis-(N-tert-butyl-benzamide)
4,4-diselenobis-(N-methyl-benzamide)
4,4-diselenobis-(N-ethyl-benzamide)
4,4-diselenobis-(N-propyl-benzamide)
4,4-diselenobis-(N-isopropyl-benzamide)
4,4-diselenobis-(N-tert-butyl-benzamide)
4,4-diselenobis-(N-benzyl-benzamide)
4,4-diselenobis-[N-(4-hydroxyphenyl)-benzamide]
4,4-diselenobis-[N-(2-hydroxy-5-methylphenyl)-benzamide]
4,4-diselenobis-[N-(4-chlorophenyl)-benzamide]
4,4-diselenobis-[N-(3-chloro-2-methoxyphenyl)-benzamide]

4,4-diselenobis-[N-(4-dimethylaminophenyl)-benzamide]
4,4-diselenobis-[N-(2-methoxy-5-nitrophenyl)-benzamide]
4,4-diselenobis-[N-(4-cyanophenyl)-benzamide]
4,4-diselenobis-[N-(2-cyanophenyl)-benzamide]
4,4-diselenobis-[N-(4-fluorophenyl)-benzamide]
4,4-diselenobis-[N-(2-trifluoromethylphenyl)-benzamide]
4,4-diselenobis-[N-(3,4-methylenedioxyphenyl)-benzamide]
2,2-diselenobis-(N-phenyl-benzamide)
2,2-diselenobis-[N-phenyl-(4-fluorobenzamide)]
2,2-diselenobis-[N-phenyl-(4-chlorobenzamide)]
2,2-diselenobis-[N-phenyl-(4-methylbenzamide)]
2,2-diselenobis-[N-phenyl-(3-methoxybenzamide)]
2,2-diselenobis-[N-phenyl-(4-trifluoromethylbenzamide)]
2,2-diselenobis-[N-phenyl-(5-chlorobenzamide)]
2,2-diselenobis-[N-phenyl-(3-nitrobenzamide)]
2,2-diselenobis-[N-phenyl-(3,4-methylenedioxybenzamide)]
2,2-diselenobis-[N-(4-nitrophenyl)-benzamide]
2,2-diselenobis-[N-(4-fluorophenyl)-benzamide]
2,2-diselenobis-[N-(4-cyanophenyl)-benzamide]
2,2-diselenobis-[N-(4-methoxycarbonylmethylphenyl)-benzamide]
2,2-diselenobis-N-[4-(1-ethoxycarbonylethyl)-phenyl]-benzamide]
2,2-diselenobis-[N-(4-trifluoromethylphenyl)-benzamide]
2,2-diselenobis-[N-(4-methylphenyl)-benzamide]
2,2-diselenobis-[N-(4-methoxyphenyl)-benzamide]
2,2-diselenobis-[N-(4-chlorophenyl)-benzamide]
2,2-diselenobis-[N-(4-dimethylaminophenyl)-benzamide]
2,2-diselenobis-[N-(2-hydroxyphenyl)-benzamide]
2,2-diselenobis-[N-(2-methoxyphenyl)-benzamide]
2,2-diselenobis-[N-(2-methoxycarbonylphenyl)-benzamide]
2,2-diselenobis-[N-(2-carboxyphenyl)-benzamide]
2,2-diselenobis-[N-(3-hydroxyphenyl)-benzamide]
2,2-diselenobis-[N-(4-hydroxyphenyl)-benzamide]
2,2-diselenobis-[N-(2-nitrophenyl)-benzamide]
2,2-diselenobis-[N-(2-chlorophenyl)-benzamide]
2,2-diselenobis-[N-(3,4-dimethoxyphenyl)-benzamide]
2,2-diselenobis-[N-(3,4-methylenedioxyphenyl)-benzamide]
2,2-diselenobis-(N-benzyl-benzamide)
2,2-diselenobis-[N-(4-phenylbutyl)-benzamide]
2,2-diselenobis-(N-cyclohexyl-benzamide
2,2-diselenobis-(N-cyclohexylmethyl-benzamide
2,2-diselenobis-(N-methyl-benzamide)
2,2-diselenobis-(N-ethyl-benzamide)
2,2-diselenobis-(N-propyl-benzamide)
2,2-diselenobis-(N-isopropyl-benzamide)
2,2-diselenobis-(N-n-butyl-benzamide)
2,2-diselenobis-(N-tert-butyl-benzamide)
2,2-diselenobis-(N-hexyl-benzamide)
2,2-diselenobis-(N-octyl-benzamide)
2,2-diselenobis-(N-dodecyl-benzamide)
2,2-diselenobis-(N-hexadecyl-benzamide)
2,2-diselenobis-(N-octadecyl-benzamide)

The substances of the present invention exhibit glutathione-peroxidase-like properties and thus are able to replace this enzyme and to prevent in this way in cooperation with a mercaptane the harmful effect of active oxygen metabolites.

The selenium dependent glutathione (GSH)-peroxidase (Px) catalyses the reduction of $H_2O_2$ and of organic hydroperoxides:

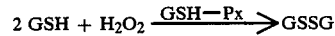

$$2\ GSH + H_2O_2 \xrightarrow{GSH-Px} GSSG$$

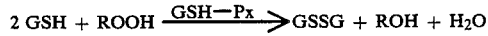

$$2\ GSH + ROOH \xrightarrow{GSH-Px} GSSG + ROH + H_2O$$

The selenium containing enzyme protects the cells against the peroxidation and plays an important role in the modulation of the arachidonic acid metabolism (C. C. Reddy, E. J. Massaro, Fundam. and Appl. Toxicology (3), 9–10 (1983), pages 431–436, and L. Flohé in Free Radicals in Biology, Vol. V, Edited by W. A. Pryor, 1982, Academic Press, pages 223–254).

The glutathione-peroxidase plays a role in all diseases wherein a cell injury of the respective tissue and finally a necrose results due to an increased formation of active oxygen metabolites in form of peroxides (such as lipoid peroxides and hydrogen peroxide). This so-called "oxidative stress" for example can be seen in liver diseases—induced by inflammative or autoimmunologic reactions, by alcohol or by medicaments—but also in other diseases, for example the cardiac infarction. It is known, that after a cardiac infarction, leucocytes migrate into the injured area and the cell destruction is accompanied by an increased release of the above named active oxygen metabolites. Finally, this leads to a progressive decomposition of the tissue.

In such cases, the important and naturally existing protecting system consisting of various, peroxides and active oxygen decompositing enzymes, is overloaded. This includes superoxide dismutase, catalase, and in particular the glutathione-redox system with the respective enzyme component glutathione-peroxidase. The latter principle is of a great importance, since it is capable of depoisoning both organic peroxides and hydrogen peroxide. It is confirmed that this system plays an important role for the intact liver function (Wendel et al, Biochemical Pharmacology, Vol. 31, page 361 (1982)) and that for example the extent of an experimental liver injury is dependent on this system, i.e. on the content of the liver of glutathione on one side and of the activity of the enzyme glutathione-peroxidase on the other side. In the course of a generic inflammation, this liver protection mechanism is essentially reduced (Bragt et al, Agents and Actions, Supp. 17, page 214 (1980)), whereby the liver suffers from an essentially increased "oxidative stress".

A very important role is played by the reactive oxygen metabolites as mediators of inflammations. They seem to take part in leucotaxis, vessel permeability, injuries of connective tissues and immunocomplex, complement-induced effects as well as in injuries caused by reflowing into ischemic areas (L. Flohé et al, The Pharmacology of Inflammation, ed. I. L., Bonta et al, Handbook of Inflammation, Vol. 5, Elsevier, Amsterdam, pages 255–270).

Also the injuries after ionising radiation are caused by the formation of radicals and of active oxygen metabolites. A route for the chemical cytoprotection therefore is a strengthening of the glutathione/glutathione-peroxidase-system (H. Rink in "Glutathione": Proceeding of the 16th Conference of the German Society of Biological Chemistry, 1973, edited by Flohé, Benöhr, Sies, Walter and Wendel, page 206).

The measuring of the glutathione-peroxidase-like activity was carried out according to the method of A. Wendel (A. Wendel, Methods in Enzymology, Vol. 77, 325-333 (1981)). In this experiment, the disparation of GSH in the presence of t-butylhydroperoxide is measured. Surprisingly, it has now been found that the compounds of the present invention of the formula (I) possess a glutathione-peroxidase-like activity.

Glutathione-peroxidase-like activity

In in vitro-experiments, the catalysis of the peroxidase decomposition has been examined. It was found, that the compounds of the present invention can replace the glutathione-peroxidase.

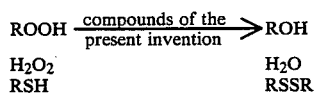

The catalytic activity is expressed in GSH-Px units. As a reference substance, Ebselen, 2-phenyl-1,2-benzisoselenazole-3(2H)-one was used (A. Wendel, M. Fansel, H. Safayhi, G. Tiegs, R. Otter, Biochem. Pharmac. 33, 3241, 1984).

For comparative purposes, the activity of Ebselen was taken as 100% and the activity of the compounds of the present invention was based on that of Ebselen.

Ebselen was used in a concentration of 30 μmole, as dissolving agent DMF was used. The diselenides were used in a concentration of 15 μmole (dimethylformamide), since in the diselenides, 2 selenium atoms per mole are present.

| Substance | Catalytic activity (in %) |
|---|---|
| Ebselen | 100 |
| 2,2-diselenobis-(N—dimethyl-benzamide) | 180 |
| 2,2-diselenobis-(N—diisopropyl-benzamide) | 200 |
| 2,2-diselenobis-(N—pentamethylene-benzamide) | 125 |
| 2,2-diselenobis-(N—methyl-N—phenyl-benzamide) | 225 |
| 3,3-diselenobis-(N—dimethyl-benzamide) | 220 |
| 2,2-diselenobis-(benzanilide) | 105 |
| 2,2-diselenobis-(N—benzyl-benzamide) | 105 |
| 2,2-diselenobis-[N—(trifluoromethylphenyl)-benzamide] | 100 |
| 2,2-diselenobis-(N—cyclohexylmethyl-benzamide) | 90 |
| 2,2-diselenobis-[N—(3-hydroxyphenyl)-benzamide] | 115 |
| 2,2-diselenobis-[N—(3,5-dichlorophenyl)-benzamide] | 85 |
| 2,2-diselenobis-(N—methyl-benzamide) | 110 |

The compounds of the present invention may be prepared for instance by a process wherein diselenobis-benzoic acids of the general formula (II)

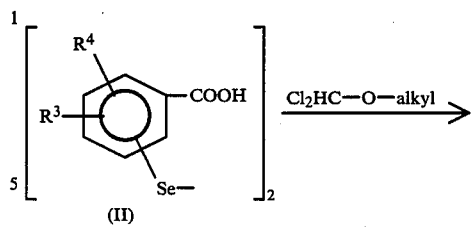

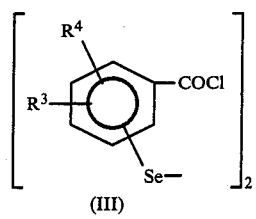

wherein $R^3$, $R^4$ have the meanings given in formula (I) and wherein the diseleno bridge is present in ortho-, meta- or para-position, in a suitable solvent are reacted with dichloromethylalkylethers, such as dichloromethylmethylether, dichloromethylbutylether, in the presence of zinc chloride for about 72 hours or less at room temperature to the corresponding acid chlorides of the general formula (III) which, after their isolation, are reacted with amines of the general formula (IV)

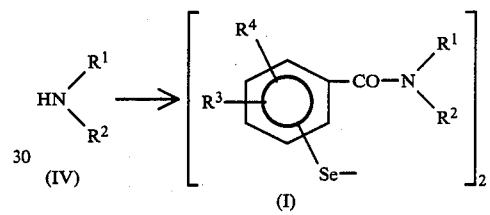

wherein $R^1$, $R^2$ have the meanings given in formula (I) to form compounds of the formula (I) in a manner known per se. The diselenobis-benzoic acid used as starting substances can be prepared according to various methods.

Method 1 (A. Ruwet, M. Renson, Bull. Soc. Chim. Belg. 75, 157-163 (1966))

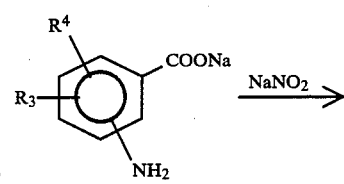

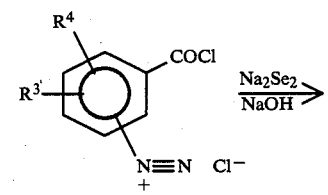

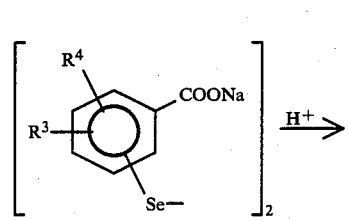

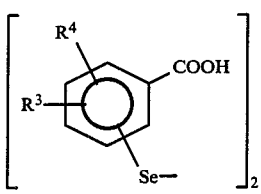

The yields of this reaction are good (90% of the theory) as far as 2-aminobenzoic acids are concerned and they are satisfactory for substituted 2-aminobenzoic acids. By using 3- and 4-aminobenzoic acids, only very low yields are obtained.

Method 2 (W. R. Gaythwaite, J. Kenyon, H. Phillips, J. Chem. Soc. 2280 (1928) and J. W. Baker, E. F. C. Banett, W. T. Tweed, J. Chem. Soc. 2831 (1952))

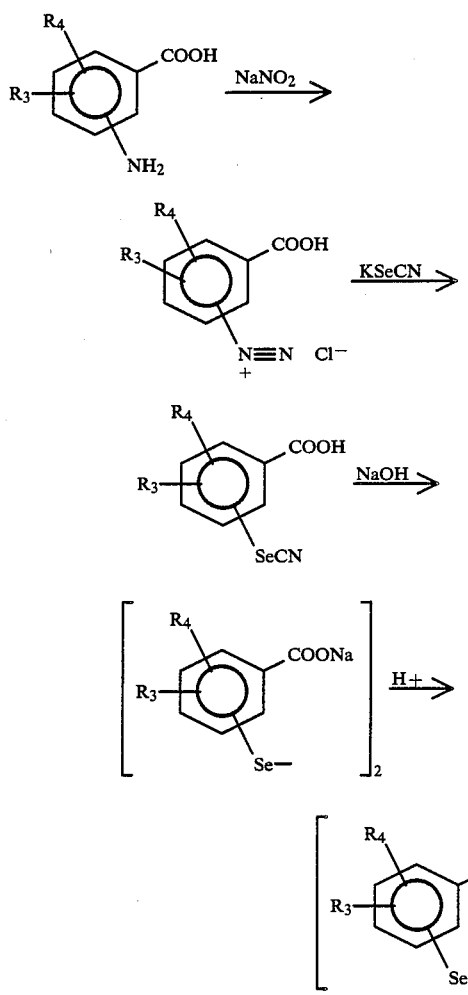

According to this method, also 3,3- and 4,4-diselenobenzoic acids can be obtained in better yields.

The amines used for the reaction are known compounds, such as dimethylamine, diethylamine, dipropylamine, diisopropylamine, di-n-butylamine, diisobutylamine, di-n-hexylamine, di-n-heptylamine, di-n-octylamine, di-n-decylamine, di-n-dodecylamine, N-n-butyl-methylamine, N-n-butylethylamine, N-tert-butyl-methylamine, N-cyclohexyl-methylamine, N-cyclopentyl-methylamine, N-cyclooctyl-methylamine, N-benzylmethylamine, N-ethylbenzylamine, N-methylaniline, N-ethylaniline, N-methyl-p-anisidine, N-ethyl-m-toluidine, N-ethyl-2-nitroaniline, pyrrolidine, piperidine, methylamine, ethylamine, propylamine, isopropylamine, tert-butylamine, cyclopropylamine, cyclobutylamine, cyclopentylamine, cyclohexylamine, cyclooctylamine, cyclopropylmethylamine, cyclohexylmethylamine, cycloheptylmethylamine, cyclooctylmethylamine, n-pentylamine, n-hexylamine, n-heptylamine, n-octylamine, n-decylamine, n-dodecylamine, n-hexadecylamine, n-octadecylamine, benzylamine, 4-aminophenol, 3-aminophenol, 2-aminophenol, 2-amino-4-methylphenol, 4-amino-3-methylphenol, 2-amino-5-methylphenol, 4-amino-2,6-dichlorophenol, 4-amino-2,6-dimethylphenol, 4-chloroaniline, 2-chloroaniline, 4-bromoaniline, 3-chloro-2-methoxyaniline, 2-chloro-5-methoxyaniline, N,N-dimethyl-p-phenylenediamine, 4-methoxy-2-methylaniline, 2-methoxy-5-nitroaniline, 4-cyanoaniline, 3-cyanoaniline, 2-cyanoaniline, 2-cyano-4-nitroaniline, 4-fluoroaniline, 2-fluoroaniline, 2-fluoro-5-nitroaniline, 4-trifluoromethylaniline, 2-trifluoromethylaniline, 3,4-methylenedioxyaniline.

A further possibility for the preparation of the compounds of the present invention is to react benzisoelenazolones of the formula (V), wherein $R^2$, $R^3$, $R^4$ have the meanings given in formula (I), which can be obtained according to the processes of DE-OS 30 27 073=U.S. Pat. No. 4,352,799 and DE-OS No. 30 27 075=U.S. Pat. No. 4,418,069, respectively, with an approximately equimolecular amount of a mercaptane, such as ethylmercaptane, in a suitable organic solvent at room temperature, to form intermediate compounds of the formula (VI)

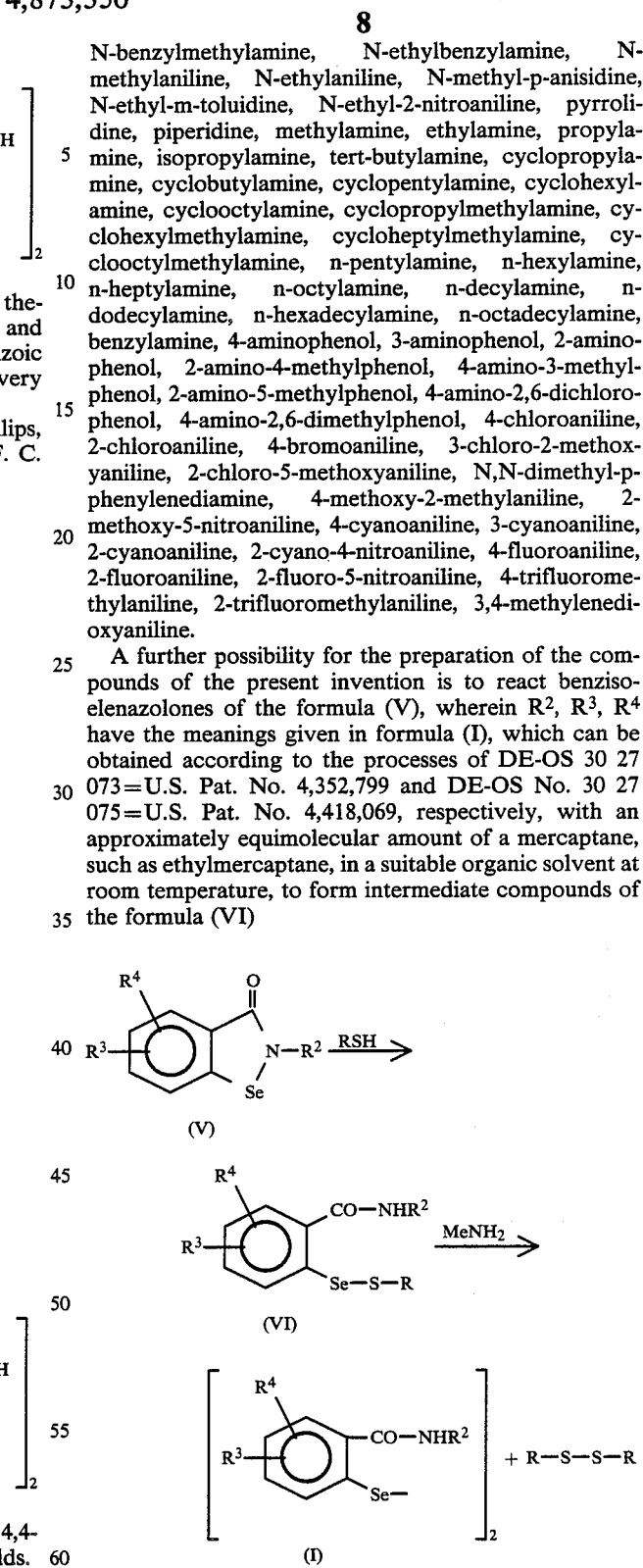

which in the presence of an amine, such as methylamine, easily can be converted into the compounds of the present invention of formula (I) by disproportion.

The present invention also refers to pharmaceutical preparations containing compounds of the formula (I). The pharmaceutical preparations of the present invention are those for the enteric like oral or rectal as well as the parenteric administration containing the pharmaceutically active compounds alone or together with a common pharmaceutically acceptable carrier. Conveniently, the pharmaceutical preparation of the active component is present in form of single doses adapted to the desired administration, such as tablets, dragees, capsules, suppositories, granulates, solutions, emulsions or suspensions. The dosage of the substances normally lies between 10 and 1000 mg per day, preferably between 30 and 300 mg per day, and the administration can be made in a single dose or in a plurality of partial doses, preferably in two to three partial doses per day.

The preparation of the compounds of the present invention is illustrated in detail in the following examples. The melting points indicated therein were measured using a Büchi 510-melting point measurement apparatus and are indicated in centigrades and not corrected.

General prescription for the preparation of diselenobisbenzoic acid chlorides with the example of the 2,2-diselenobis-benzoic acid.

20 g (50 mmole) of 2,2-diselenobis-benzoic acid are suspended in 400 ml of dry dichloromethane. To this mixture 45 ml (500 mmole) of dichloromethylmethylether and 1 g of dry zinc chloride are added. The reaction mixture is stirred for 72 hour at room temperature. After filtration of the residue the solution is concentrated. The acid chloride is recrystallized from toluene. 6 g of the pure product are obtained. By partial concentration of the mother liquor further 4,6 g are obtained.

Yield: 10,6 g (48,5% of the theory); m.p. 170° C.

EXAMPLE 1

2,2-Diselenobis-(N-dimethyl-benzamide)

4,0 g (9,15 mmole) of 2,2-diselenobis-benzoic acid chloride are dissolved in 50 ml of diisopropylether. This solution is added dropwise to a 40% solution of dimethylamine in water (10 ml) while stirring. After stirring for 15 minutes 100 ml of water are added to the mixture, the precipitate is filtered and washed with 50 ml of water. The precipitate is dried and recrystallized from toluene/hexane.

Yield: 3,1 g (75% of the theory); m.p. 173°–174° C.

EXAMPLE 2

2,2-Diselenobis-(N-diisopropyl-benzamide)

4,0 g (9,15 mmole) of 2,2-diselenobis-benzoic acid chloride are dissolved in 50 ml of pyridine. This solution is added dropwise to a solution of 2,0 g (19,8 mmole) of diisopropylamine in 20 ml of pyridine. It is stirred for further 15 minutes and the solution is poured into a mixture of ice, water and diluted hydrochloric acid (about 250 ml). The precipitate is filtered, washed with water and dried.

Yield: 4,1 g (93,3% of the theory), m.p. 156°–158° C.

EXAMPLE 3

2,2-Diselenobis-(N,N-pentamethylene-benzamide)

Similar to example 2 from:
4,0 g (9,15 mmole) of 2,2-diselenobis-benzoic acid chloride
2,0 g (23,5 mmole) of piperidine.
Yield: 3,8 g (77,7% of the theory); m.p. 159°–160° C.

EXAMPLE 4

2,2-Diselenobis-(N-benzyl-N-methyl-benzamide)

Similar to example 2 from:
4,0 g (9,15 mmole) of 2,2-diselenobis-benzoic acid chloride
2,4 g (19,8 mmole) of N-benzylmethylamine.
Yield: 2,9 g (52,3% of the theory); m.p. 139°–140° C.

EXAMPLE 5

2,2-Diselenobis-(N-methyl-N-phenyl-benzamide)

Similar to example 2 from:
4,0 g (9,15 mmole) of 2,2-diselenobis-benzoic acid chloride
2,2 g (20,6 mmole) of N-methylaniline.
Yield: 3,8 g (71,85% of the theory); m.p. 83° C.

EXAMPLE 6

3,3-Diselenobis-(N-dimethyl-benzamide)

Similar to example 1 from:
5,46 g (12,49 mmole) of 3,3-diselenobis-benzoic acid chloride
10 ml of a 40% aqueous dimethylamine solution.
Yield: 2,8 g (49,4% of the theory); m.p. 165°–167° C.

EXAMPLE 7

4,4-Diselenobis-(N-dimethyl-benzamide)

Similar to example 1 from:
4,0 g (9,15 mmole) of 4,4-diselenobis-benzoic acid chloride
10 ml of a 40% aqueous dimethylamine solution.
Yield: 3,2 g (77% of the theory); m.p. 180°–182° C.

EXAMPLE 8

3,3-Diselenobis-(N-phenyl-benzamide)

2,0 g (4,6 mmole) of 3,3-diselenobis-benzoic acid chloride are dissolved in 20 ml of dry pyridine. To this solution 0,9 g (9,6 mmole) of aniline in 10 ml of pyridine are added dropwise. The solution is stirred for further 15 minutes and then given into a mixture of ice, water and diluted hydrochloric acid. The precipitate is filtered, washed with water and dried. After recrystallisation from dimethylformamide, 1,72 g (68% of the theory) are obtained.
m.p. 209°–212° C.

EXAMPLE 9

3,3-Diselenobis-(N-methyl-benzamide)

Similar to example 1 from:
2 g (4,6 mmole) of 3,3-diselenobis-benzoic acid chloride
5 ml of a 40% aqueous methylamine solution.
Yield: 1 g (55% of the theory); m.p. 172° C.

EXAMPLE 10

3,3-Diselenobis-[N-(4-hydroxyphenyl)-benzamide]

Similar to example 8 from:
2 g (4,6 mmole) of 3,3-diselenobis-benzoic acid chloride
1,0 g (9,17 mmole) of 4-aminophenol.
Yield: 0,93 g (35% of the theory); m.p. 268°–270° C.

EXAMPLE 11

4,4-Diselenobis-(N-phenyl-benzamide)

Similar to example 8 from:
2 g of 4,4-diselenobis-benzoic acid chloride
0,8 g of aniline.
Yield: 1,43 g (57% of the theory). m.p. 271°–274° C.

EXAMPLE 12

4,4-Diselenobis-[N-(4-fluorophenyl)-benzamide]

Similar to example 8 from:
2 g of 4,4-diselenobis-benzoic acid chloride
1,0 g of 4-fluoroaniline.
Yield: 1,51 g (56,5% of the theory); m.p. 265°–268° C.

EXAMPLE 13

4,4-Diselenobis-(N-tert-butyl-benzamide)

Similar to example 8 from:
2 g of 4,4-diselenobis-benzoic acid chloride
0,8 g of tert-butylamine.
Yield: 1 g (44,3% of the theory); m.p. 212°–215° C.

EXAMPLE 14

4,4-Diselenobis-(N-methyl-benzamide)

Similar to example 8 from:
2 g of 4,4-diselenobis-benzoic acid chloride
5 ml of a 40% aqueous methylamine solution.
Yield: 0,8 g (44% of the theory)

EXAMPLE 15

2,2-Diselenobis-(N-diphenyl-benzamide)

Similar to example 2 from:
4,0 g of 2,2-diselenobis-benzoic acid chloride
3,3 g of diphenylamine.

EXAMPLE 16

2,2-diselenobis-(N-benzyl-N-phenyl-benzamide)

Similar to example 2 from:
4,0 g of 2,2-diselenobis-benzoic acid chloride
3,4 g of N-benzylaniline.
Yield: 3,2 g (47,9% of the theory); m.p. 242°–244° C.

EXAMPLE 17

2,2-Diselenobis-[N-(4-methoxyphenyl)-N-methyl-benzamide]

Similar to example 2 from:
4,0 g of 2,2-diselenobis-benzoic acid chloride
3,3 g of 4-methoxy-N-methylaniline.
Yield: 2,9 g (49,7% of the theory); m.p. 218°–220° C.

EXAMPLE 18

2,2-Diselenobis-[N-ethyl-(4-fluorophenyl)-benzamide]

Similar to example 2 from:
4,0 g of 2,2-diselenobis-benzoic acid chloride
3,3 g of N-ethyl-4-fluoroaniline.
Yield: 3,5 g (57,8% of the theory); m.p. 132°–133° C.

EXAMPLE 19

2,2-Diselenobis-[N-ethyl-(3-methylphenyl)-benzamide]

Similar to example 2 from:
4,0 g of 2,2-diselenobis-benzoic acid chloride
3,3 g of N-ethyl-m-toluidine.
Yield: 3,2 g (55% of the theory); m.p. 120°–121° C.

EXAMPLE 20

2,2-Diselenobis-[N-methyl-(3-methylphenyl)-benzamide]

Similar to example 2 from:
4,0 g of 2,2-diselenobis-benzoic acid chloride
3,4 g of N-methyl-m-toluidine.
Yield: 3,0 g (54,1% of the theory); m.p. 113°–115° C.

EXAMPLE 21

2,2-Diselenobis-[N-methyl-(2-methoxycarbonylphenyl)-benzamide]

Similar to example 2 from:
4,0 g of 2,2-diselenobis-benzoic acid chloride
3,9 g of N-methyl-anthranilic acid methylester.
Yield: 2,8 g (44,1% of the theory); m.p. 104°–105° C.

GENERAL PRESCRIPTION 5 mmole of a 2-substituted 1,2-benzoisoselenoazole-3(2H)-one are suspended in about 200 ml of methanol and 5,5 mmole of a mercaptane (for example ethylmercaptane) are added. After several minutes (5–15 min) a clear colution is obtained. By means of thin layer chromatography it is checked whether the 1,2-benzoisoselenoazole-3(2H)-one has reacted completely. If this is the case, 2 ml of a 33% aqueous solution of methylamine are added. The reaction mixture is stirred for at least one hour. The obtained precipitate is sucked off, washed with methanol and finally with ether. In some cases it is still stirred in methylene chloride. If necessary, the thus obtained diselenide can be recrystallized from a suitable solvent.

*In some cases the intermediate product after several minutes crystallizes again. In these cases to the reaction mixture as much as dimethylformamide is added until a clear solution is obtained again.

EXAMPLE 22

2,2-Diselenobis-[N-(4-nitrophenyl)-benzamide]

Similar to the general prescription from:
1,0 g (3,13 mmole) of 2-(4-nitrophenyl)-1,2-benzoisoselenoazole-3(2H)-one
0,5 ml of ethylmercaptane
1,5 ml of 33% methylamine
in 100 ml of methanol.
Yield: 0,65 g (65% of the theory); m.p. 243°–254° C.

EXAMPLE 23

2,2-Diselenobis-[N-(3-hydroxyphenyl)-benzamide]

Similar to example 22 from:
5 g of 2-(3-hydroxyphenyl)-1,2-benzoisoselenoazole-3(2H)-one
1,3 ml of ethylmercaptane
4,3 ml of 33% methylamine
in 250 ml of methanol.
Yield: 1,2 g (12% of the theory); m.p. 285°–286° C.

EXAMPLE 24

2,2-Diselenobis-[N-(4-hydroxyphenyl)-benzamide]

Similar to example 22 from:
2,5 g of 2-(4-hydroxyphenyl)-1,2-benzoisoselenoazole-3(2H)-one
2,0 ml of 33% methylamine
0,65 ml of ethylmercaptane
in 100 ml of methanol.
Yield: 1,15 g (46% of the theory); m.p. 282°–284° C.

EXAMPLE 25

2,2-Diselenobis-[N-(2-hydroxyphenyl)-benzamide]

Similar to example 22 from:
3 g of 2-(2-hydroxyphenyl)-1,2-benzoisoselenoazole-3(2H)-one
0,78 ml of ethylmercaptane
3 ml of 33% methylamine
in 100 ml of methanol.
Yield: 0,5 g (8,3% of the theory); m.p. 235°–238° C.

EXAMPLE 26

2,2-Diselenobis-(N-cyclohexylmethyl)-benzamide

Similar to example 22 from:
2,5 g of 2-cyclohexylmethyl-1,2-benzoisoselenoazole-3(2H)-one
0,53 ml of ethylmercaptane
2,1 ml of 33% methylamine
in 100 ml of methanol.
Yield: 2,15 g (86% of the theory); m.p. 227°–229° C.

EXAMPLE 27

2,2-Diselenobis-[N-(2-trifluoromethyl)-benzamide]

Similar to example 22 from:
1 g of 2-(2-trifluoromethylphenyl)-1,2-benzoisoselenoazole-3(2H)-one
0,215 ml of ethylmercaptane
0,73 ml of 33% methylamine
in 50 ml of methanol.
Yield: 0,508 g (51,2% of the theory); m.p. 235°–236° C.

EXAMPLE 28

2,2-Diselenobis-N-[4-(1-ethoxycarbonylethyl)-phenyl]-benzamide

Similar to example 22 from:
0,7 g of 2-[4-(1-ethoxycarbonylethyl)-phenyl]-1,2-benzoisoselenoazole-3(2H)-one
0,14 ml of ethylmercaptane
0,68 ml of 33% methylamine
in 50 ml of methanol.
Yield: 0,1 g (14,3% of the theory); m.p. 179°–181° C.

EXAMPLE 29

2,2-Diselenobis-[N-(3,4-methylendioxyphenyl)-benzamide]

Similar to example 22 from:
0,82 g of 2-(3,4-methylendioxyphenyl)-1,2-benzoisoselenoazole-3(2H)-one
0,19 ml of ethylmercaptane
0,94 ml of 33% methylamine
in 50 ml of methanol.
Yield: 0,7 g (85,4% of the theory); m.p. 270°–272° C.

EXAMPLE 30

2,2-Diselenobis-[N-(4-dimethylaminophenyl)-benzamide]

Similar to example 22 from:
2 g of 2-(4-dimethylaminophenyl)-1,2-benzoisoselenoazole-3(2H)-one
0,46 ml of ethylmercaptane
1,18 ml of 33% methylamine
in 100 ml of methanol.
Yield: 1 g (49,8% of the theory); m.p. 258°–260° C.

EXAMPLE 31

2,2-Diselenobis-[N-(4-trifluoromethylphenyl)-benzamide]

Similar to example 22 from:
2 g of 2-(4-trifluoromethylphenyl)-1,2-benzoisoselenoazole-3(2H)-one
0,428 ml of triethylamine
1,45 ml of 33% methylamine
in 100 ml of methanol.
Yield: 0,87 g (43,8% of the theory); m.p. 273° C.

EXAMPLE 32

2,2-Diselenobis-[N-(4-methylphenyl)-benzamide]

Similar to example 22 from:
2 g of 2-(4-methylphenyl)-1,2-benzoisoselenoazole-3(2H)-one
0,5 ml of ethylmercaptane
1,73 ml of 33% methylamine
in 100 ml of methanol.
Yield: 1,44 g (71,8% of the theory); m.p. 255° C.

EXAMPLE 33

2,2-Diselenobis-(N-benzyl-benzamide)

Similar to example 22 from:
2 g of 2-benzyl-1,2-benzoisoselenoazole-3(2H)-one
0,5 ml of ethylmercaptane
1,73 ml of 33% methylamine
in 100 ml of methanol.
Yield: 1,37 g (68,4% of the theory); m.p. 196°–198° C.

EXAMPLE 34

2,2-Diselenobis-[N-(4-methoxyphenyl)-benzamide]

Similar to example 22 from:
2 g of 2-(4-methoxyphenyl)-1,2-benzoisoselenoazole-3(2H)-one
0,48 ml of ethylmercaptane
1,6 ml of 33% methylamine
in 150 ml of methanol.
Yield: 1,26 g (63,2% of the theory); m.p. 290°–292° C.

EXAMPLE 35

2,2-Diselenobis-[N-(4-chlorophenyl)-benzamide]

Similar to example 22 from:
2 g of 2-(4-chlorophenyl)-1,2-benzoisoselenazole-3(2H)-one
0,48 ml of ethylmercaptane
0,53 ml of 33% methylamine
in 150 ml of methanol.
Yield: 1,45 g (72% of the theory); m.p. 280°–283° C.

EXAMPLE 36

2,2-Diselenobis-[N-(4-phenylbutyl)-benzamide]

Similar to example 22 from:
2 g of 2-(4-phenylbutyl)-1,2-benzoisoselenoazole-3(2H)-one
0,45 ml of ethylmercaptane
1,5 ml of 33% methylamine
in 150 ml of methanol.
Yield: 1,8 g (90% of the theory); m.p. 180°–181° C.

EXAMPLE 37

2,2-Diselenobis-[N-(3,5-dichlorophenyl)-benzamide]

Similar to example 22 from:

1,7 g of 2-(3,5-dichlorophenyl)-1,2-benzoisoselenoazole-3(2H)-one
0,4 ml of ethylmercaptane
0,5 ml of 33% methylamine
in 200 ml of methanol.
Yield: 2,9 g (84% of the theory); m.p. 255°–257° C.

EXAMPLE 38

2,2-Diselenobis-[N-(2-nitrophenyl)-benzamide]

Similar to example 22 from:
0,5 g of 2-(2-nitrophenyl)-1,2-benzoisoselenoazole-3(2H)-one
0,12 ml of ethylmercaptane
0,2 ml of 33% methylamine
in 50 ml of methanol.
Yield: 0,45 g (90% of the theory); m.p. 225° C.

EXAMPLE 39

2,2-Diselenobis-[N-(2-chlorophenyl)-benzamide]

Similar to example 22 from:
2 g of 2-(2-chlorophenyl)-1,2-benzoisoselenoazole-3(2H)-one
0,6 ml of ethylmercaptane
0,7 ml of 33% methylamine
in 150 ml of methanol.
Yield: 0,8 g (32,2% of the theory)

EXAMPLE 40

2,2-Diselenobis-(N-methyl-benzamide)

Similar to example 22 from:
1 g of 2-methyl-1,2-benzoisoselenoazole-3(2H)-one
0,35 ml of ethylmercaptane
1,2 ml of 33% methylamine
in 100 ml of methanol.
Yield: 0,65 g (63,8% of the theory); m.p. 277°–279° C.

EXAMPLE 41

2,2-Diselenobis-[N-phenyl-(5-methoxy-benzamide)]

Similar to example 22 from:
1 g of 5-methoxy-2-phenyl-1,2-benzoisoselenoazole-3(2H)-one
0,25 ml of ethylmercaptane
1 ml of 33% methylamine
in 80 ml of methanol.
Yield: 0,6 g (60% of the theory); m.p. 203°–204° C.

EXAMPLE 42

2,2-Diselenobis-[N-(4-cyanophenyl)-benzamide]

Similar to example 22 from:
2 g of 2-(2-cyanophenyl)-1,2-benzoisoselenoazole-3(2H)-one
0,5 ml of ethylmercaptane
5 ml of 33% methylamine
in 150 ml of methanol.
Yield: 0,5 g (25% of the theory); m.p. 268°–270° C.

EXAMPLE 43

2,2-Diselenobis-(N-cyclopentyl-benzamide)

Similar to example 22 from:
0,7 g of 2-cyclopentyl-1,2-benzoisoselenoazole-3(2H)-one
0,2 ml of ethylmercaptane
3 ml of 33% methylamine
in 50 ml of methanol.
Yield: 0,46 g (65,7% of the theory); m.p. 275°–280° C.

EXAMPLE 44

2,2-Diselenobis-(N-cyclohexyl-benzamide)

Similar to example 22 from:
1 g of 2-cyclohexyl-1,2-benzoisoselenoazole-3(2H)-one
0,25 ml of ethylmercaptane
3 ml of 33% methylamine
in 100 ml of methanol.
Yield: 0,5 g (50% of the theory); m.p. 315° C.

EXAMPLE 45

2,2-Diselenobis-[N-(4-fluorophenyl)-benzamide]

Similar to example 22 from:
1,26 g of 2-(4-fluorophenyl)-1,2-benzoisoselenoazole-3(2H)-one
0,3 ml of ethylmercaptane
3 ml of 33% methylamine
in 100 ml of methanol.
Yield: 1,1 g (87,3% of the theory); m.p. 260° C.

EXAMPLE 46

2,2-Diselenobis-(N-hexyl-benzamide)

Similar to example 22 from:
2 g of 2-hexyl-1,2-benzoisoselenoazole-3(2H)-one
0,52 ml of ethylmercaptane
2 ml of 33% methylamine
in 150 ml of methanol.
Yield: 1,55 g (77,5% of the theory); m.p. 163°–165° C.

EXAMPLE 47

2,2-Diselenobis-(N-tert-butyl-benzamide)

Similar to example 22 from:
1,34 g of 2-tert-butyl-1,2-benzoisoselenoazole-3(2H)-one
0,4 ml of ethylmercaptane
1,4 ml of 33% methylamine
in 100 ml of methanol.
Yield: 0,96 g (71,4% of the theory); m.p. 241°–242° C.

EXAMPLE 48

2,2-Diselenobis-(N-phenyl-benzamide)

Similar to example 22 from:
2 g of 2-phenyl-1,2-benzoisoselenoazole-3(2H)-one
0,5 ml of ethylmercaptane
4 ml of 33% methylamine
in 100 ml of methanol.
Yield: 1,8 g (90% of the theory); m.p. 263°–265° C.

EXAMPLE 49

2,2-Diselenobis-[N-(3,4-dimethoxyphenyl)-benzamide]

Similar to example 22 from:
1 g of 2-(3,4-dimethoxyphenyl)-1,2-benzoisoselenoazole-3(2H)-one
0,2 ml of ethylmercaptane
2 ml of 33% methylamine
in 150 ml of methanol.
Yield: 0,25 g (25% of the theory); m.p. 235° C.

EXAMPLE 50

2,2-Diselenobis-[N-(2-methoxyphenyl)-benzamide]

Similar to example 22 from:
2 g of 2-(2-methoxyphenyl)-1,2-benzoisoselenoazole-3(2H)-one
0,5 ml of ethylmercaptane 1,5 ml of 33% methylamine
in 100 ml of methanol.
Yield: 0,95 g (47,4% of the theory); m.p. 216°–217° C.

EXAMPLE 51

2,2-Diselenobis-[N-phenyl-(3-methoxy-benzamide)]

Similar to example 22 from:
1 g of 7-methoxy-2-phenyl-1,2-benzoisoselenoazole-3(2H)-one
0,25 ml of ethylmercaptane
1,0 ml of 33% methylamine
in 100 ml of methanol.
Yield: 0,31 g (31,6% of the theory); m.p. 152°–155° C.

EXAMPLE 52

2,2-Diselenobis-[N-(2-methoxycarbonylphenyl)-benzamide]

Similar to example 22 from:
1,66 g of 2-(2-methoxycarbonylphenyl)-1,2-benzoisoselenoazole-3(2H)-one
0,5 ml of ethylmercaptane
1,5 ml of 33% methylamine
in 100 ml of methanol.
Yield: 0,55 g (25%); m.p. 230°–231° C.

EXAMPLE 53

2,2-Diselenobis-[N-(2-carboxyphenyl)-benzamide]

Similar to example 22 from:
1,5 g of 2-(2-carboxyphenyl)-1,2-benzoisoselenoazole-3(2H)-one
0,5 ml of ethylmercaptane
1,5 ml of 33% methylamine
in 150 ml of methanol.
Yield: 0,49 g (31%); m.p. 298°–300° C.

EXAMPLE 54

2,2-Diselenobis-[N-phenyl-(3,4-dimethoxy-benzamide)]

Similar to example 22 from:
1 g of 6,7-dimethoxy-2-phenyl-1,2-benzoisoselenoazole-3-(2H)-one
0,2 ml of ethylmercaptane
3 ml of 33% methylamine
in 200 ml of methanol.
Yield: 0,55 g (55% of the theory); m.p. 235° C.

EXAMPLE 55

2,2-Diselenobis-[N-phenyl-(3-methyl-benzamide)]

Similar to example 22 from:
2 g of 7-methyl-2-phenyl-1,2-benzoisoselenoazole-3(2H)-one
0,5 ml of ethylmercaptane
2 ml of 33% methylamine
in 100 ml of methanol.
Yield: 1,5 g (25% of the theory); m.p. 290°–295° C.

EXAMPLE 56

2,2-Diselenobis-[N-tert-butyl-(3-methoxybenzamide)]

Similar to example 22 from:
2 g of 7-methoxy-2-tert-butyl-1,2-benzoisoselenoazole-3(2H)-one
0,5 ml of ethylmercaptane
2 ml of 33% methylamine.

EXAMPLE 57

2,2-Diselenobis-[N-methyl-(3-methoxy-benzamide)]

Similar to example 22 from:
2 g of 7-methoxy-2-methyl-1,2-benzoisoselenoazole-3(2H)-one
0,5 ml of ethylmercaptane
2 ml of 33% methylamine
in 100 ml of methanol.
Yield: 1,7 g (65% of the theory); m.p. 216°–217° C.

What we claim is:

1. Diselenobis-benzoic acid amides of the general formula (I):

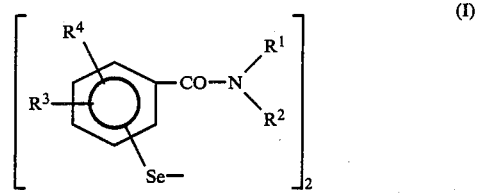

wherein:
$R^1$ and $R^2$ which are identical or different from each other, represent members selected from the group consisting of hydrogen, straight $C_{1-18}$-alkyl, branched $C_{1-18}$-alkyl, $C_{3-8}$-cycloalkyl, $C_{3-8}$-cycloalkylmethyl, phenylalkyl, phenyl, phenyl substituted by one to three substituents, identical or different from each other, selected from the group consisting of halogen, $C_{1-4}$-alkyl, $C_{1-4}$-alkoxy, hydroxy, trifluoromethyl, nitro, di-($C_{1-4}$-alkyl)-amino, cyano, carboxy, alkoxycarbonyl, alkoxycarbonylalkyl and methylenedioxy; and together a $C_4$–$C_6$-alkylene bridge, with the proviso that at least one of $R^1$ and $R^2$ is different from hydrogen, and $R^3$ and $R^4$ which are identical or different from each other, represent members selected from the group consisting of hydrogen, halogen, $C_{1-4}$-alkyl, $C_{1-4}$-alkoxy, trifluoromethyl, nitro and together methylenedioxy, the diseleno bridge in the molecule being positioned in the ortho-, meta- or para-position relative to the carbamido group.

2. Diselenobis-benzoic acid amides of formula (I) according to claim 1, wherein:
$R^1$ represents hydrogen and
$R^2$ represents a member selected from the group consisting of straight $C_{1-18}$-alkyl, branched $C_{1-18}$-alkyl, $C_{3-8}$-cycloalkyl, $C_{3-8}$-cycloalkylmethyl, benzyl, phenyl, phenyl substituted by one to three substitutents, identical or different from each other, selected from the group consisting of fluorine, chlorine, bromine, methyl, methoxy, hydroxy, trifluoromethyl, nitro, dimethylamino, cyano, carboxy, methoxycarbonyl, ethoxycarbonylethyl and, together, methylenedioxy, and $R^3$ and $R^4$ which are identical or different from each other, represent members selected from the group consisting of hydrogen, fluorine, chlorine, methyl, methoxy, trifluoromethyl, nitro and, together, methylenedioxy.

3. Diselenobis-benzoic acid amides of the general formula (I):

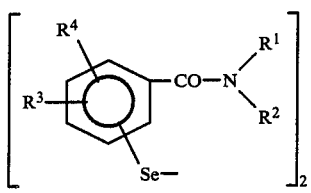

wherein:
R¹ and R² which are identical or different from each other, represent members selected from the group consisting of straight $C_{1-12}$-alkyl, $C_{5-8}$-cycloalkyl, $C_{5-8}$-cycloalkylmethyl, benzyl, phenyl, phenyl substituted by one to three substituents selected from the group consisting of methyl, methoxy and nitro; and, together, a $C_4$–$C_6$-alkylene bridge, and R³ and R⁴ which are identical or different from each other, represent a member selected from the group consisting of hydrogen, fluorine, chlorine, methyl, methoxy, trifluoromethyl and nitro,
the diseleno bridge in the molecule being positioned in the ortho-, meta- or para-position relative to the carbamido group.

* * * * *